(12) United States Patent
Kono

(10) Patent No.: US 7,710,583 B2
(45) Date of Patent: May 4, 2010

(54) SURFACE POSITION MEASURING SYSTEM, EXPOSURE METHOD AND SEMICONDUCTOR DEVICE MANUFACTURING METHOD

(75) Inventor: Takuya Kono, Yokosuka (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 373 days.

(21) Appl. No.: 11/907,190

(22) Filed: Oct. 10, 2007

(65) Prior Publication Data
US 2008/0100843 A1 May 1, 2008

(30) Foreign Application Priority Data
Oct. 11, 2006 (JP) .............................. 2006-278071

(51) Int. Cl.
*G01B 11/14* (2006.01)
(52) U.S. Cl. ...................... 356/614; 250/559.29; 355/53
(58) Field of Classification Search ......... 356/601–623; 250/548, 559.29, 559.4; 355/53, 55, 72, 355/75
See application file for complete search history.

(56) References Cited

U.S. PATENT DOCUMENTS

| | | | | |
|---|---|---|---|---|
| 5,311,288 A | * | 5/1994 | Shahar | ........................ 356/623 |
| 6,124,933 A | * | 9/2000 | Mizutani et al. | ............. 356/620 |
| 2002/0015158 A1 | * | 2/2002 | Shiode et al. | ................ 356/614 |
| 2003/0132401 A1 | * | 7/2003 | Yamada et al. | ............... 250/548 |
| 2009/0009739 A1 | * | 1/2009 | Kosugi | ......................... 355/53 |
| 2009/0116039 A1 | * | 5/2009 | Hidaka | ........................ 356/622 |

FOREIGN PATENT DOCUMENTS

| | | |
|---|---|---|
| JP | 2002-334826 | 11/2002 |
| JP | 2006-269669 | 10/2006 |

\* cited by examiner

*Primary Examiner*—Hoa Q Pham
(74) *Attorney, Agent, or Firm*—Finnegan, Henderson, Farabow, Garrett & Dunner, L.L.P.

(57) ABSTRACT

There is provided a surface position measuring system which includes a reflectivity computing module which computes predictive reflectivities of a plurality of circuit patterns, an inspection light source which irradiates an inspection light onto each of a plurality of inspection areas, area by area, above the plurality of circuit patterns under irradiation conditions determined based on a corresponding each of the predictive reflectivities of the plurality of circuit patterns, and a photodetector which detects a reflected inspection light reflected from each of the plurality of inspection areas to detect a surface position of a corresponding each of the plurality of inspection areas.

20 Claims, 5 Drawing Sheets

| | Angle of incidence | Wavelength | Intensity | Irradiation range |
|---|---|---|---|---|
| Inspection area A | a | b | c | (X1, Y1) – (X2, Y2) |
| Inspection area B | | | | |
| Inspection area C | | | | |
| Inspection area D | | | | |

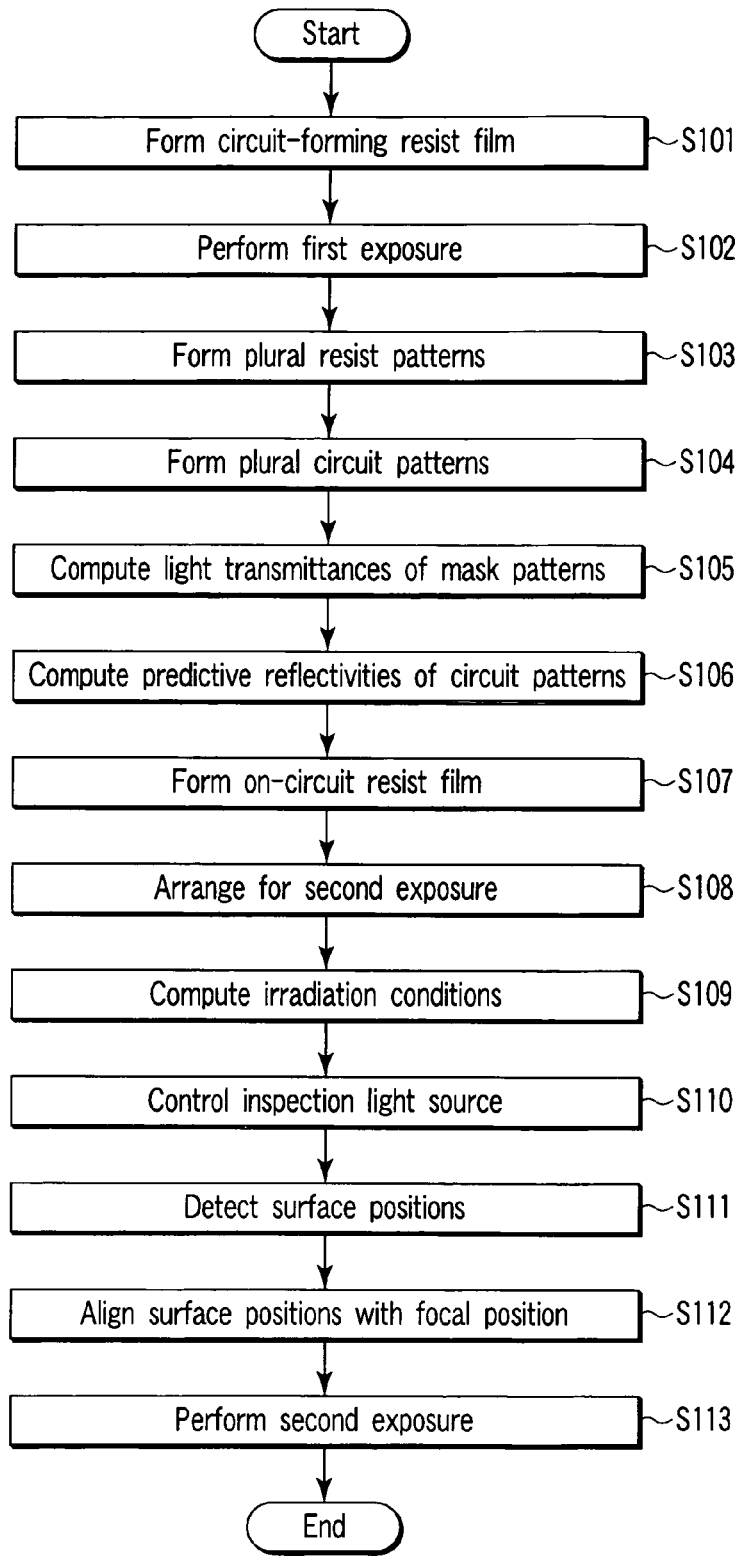
F I G. 8

SURFACE POSITION MEASURING SYSTEM, EXPOSURE METHOD AND SEMICONDUCTOR DEVICE MANUFACTURING METHOD

CROSS-REFERENCE TO RELATED APPLICATIONS

This application is based upon and claims the benefit of priority from prior Japanese Patent Application No. 2006-278071, filed Oct. 11, 2006, the entire contents of which are incorporated herein by reference.

BACKGROUND OF THE INVENTION

1. Field of the Invention

The present invention relates to a lithography technology, and more particularly to a surface position measuring system, an exposure method and a semiconductor device manufacturing method.

2. Description of the Related Art

In fabricating semiconductor devices, the images of mask patterns formed on a photomask are projected onto a resist film by using an exposure apparatus. In fabricating fine semiconductor devices, it is essential to form the projection images of the mask patterns at exact positions on the resist film. To this end, it is essential that the resist film onto which the images of the mask patterns are projected be exactly positioned at a focal point of the projection optical system of the exposure apparatus. The position of the resist film located is detected in such a manner that inspection light is applied to the resist film and the light reflected from the resist film is analyzed (for example, Jpn. Pat. Appln. KOKAI Publication No. 2002-334826). When a plurality of metal wiring patterns are laid out under the resist film, the different reflectivities of the metal wiring patterns adversely affect the detection of the position of the resist film by the inspection light.

BRIEF SUMMARY OF THE INVENTION

According to a first aspect of the present invention, there is provided a surface position measuring system comprising:

a reflectivity computing module which computes predictive reflectivities of a plurality of circuit patterns;

an inspection light source which irradiates an inspection light onto each of a plurality of inspection areas, area by area, above the plurality of circuit patterns under irradiation conditions determined based on a corresponding each of the predictive reflectivities of the plurality of circuit patterns; and a photodetector which detects a reflected inspection light reflected from each of the plurality of inspection areas to detect a surface position of a corresponding each of the plurality of inspection areas.

According to a second aspect of the present invention, there is provided an exposure method comprising:

projecting images of a plurality of mask patterns provided on a photomask onto a circuit-forming resist film provided on a wafer;

developing the circuit-forming resist film to form a plurality of resist patterns on the wafer;

forming a plurality of circuit patterns on the wafer, with use of the plurality of resist patterns;

obtaining predictive reflectivities of the plurality of circuit patterns;

forming an on-circuit resist film on the plurality of circuit patterns;

irradiating an inspection light to each of a plurality of inspection areas, area by area, of the on-circuit resist film, which are above the plurality of circuit patterns, under irradiation conditions determined based on a corresponding each of the predictive reflectivities of the plurality of circuit patterns, detecting a reflected inspection light reflected from each of the plurality of inspection areas, detecting a surface position of each of the plurality of inspection areas to a projection optical system of an exposure apparatus which irradiates an illumination light to expose the on-circuit resist film, based on the reflected inspection light reflected from a corresponding each of the plurality of inspection areas, moving the wafer to position each of the surface positions of the plurality of inspection areas at a focal point of the projection optical system of the exposure apparatus, and irradiating an illumination light to expose the on-circuit resist film.

According to a third aspect of the present invention, there is provided a semiconductor device manufacturing method of manufacturing a semiconductor device, in which the exposure method recited in the second aspect of the present invention is used.

BRIEF DESCRIPTION OF THE SEVERAL VIEWS OF THE DRAWING

FIG. 8 is a flow chart showing an exposure method according to the embodiment of the present invention.

DETAILED DESCRIPTION OF THE INVENTION

Embodiments of the present invention will be described in detail with reference to the accompanying drawings. Throughout the drawings, the same or like reference symbols designate the same or like parts and portions.

Figure 1:
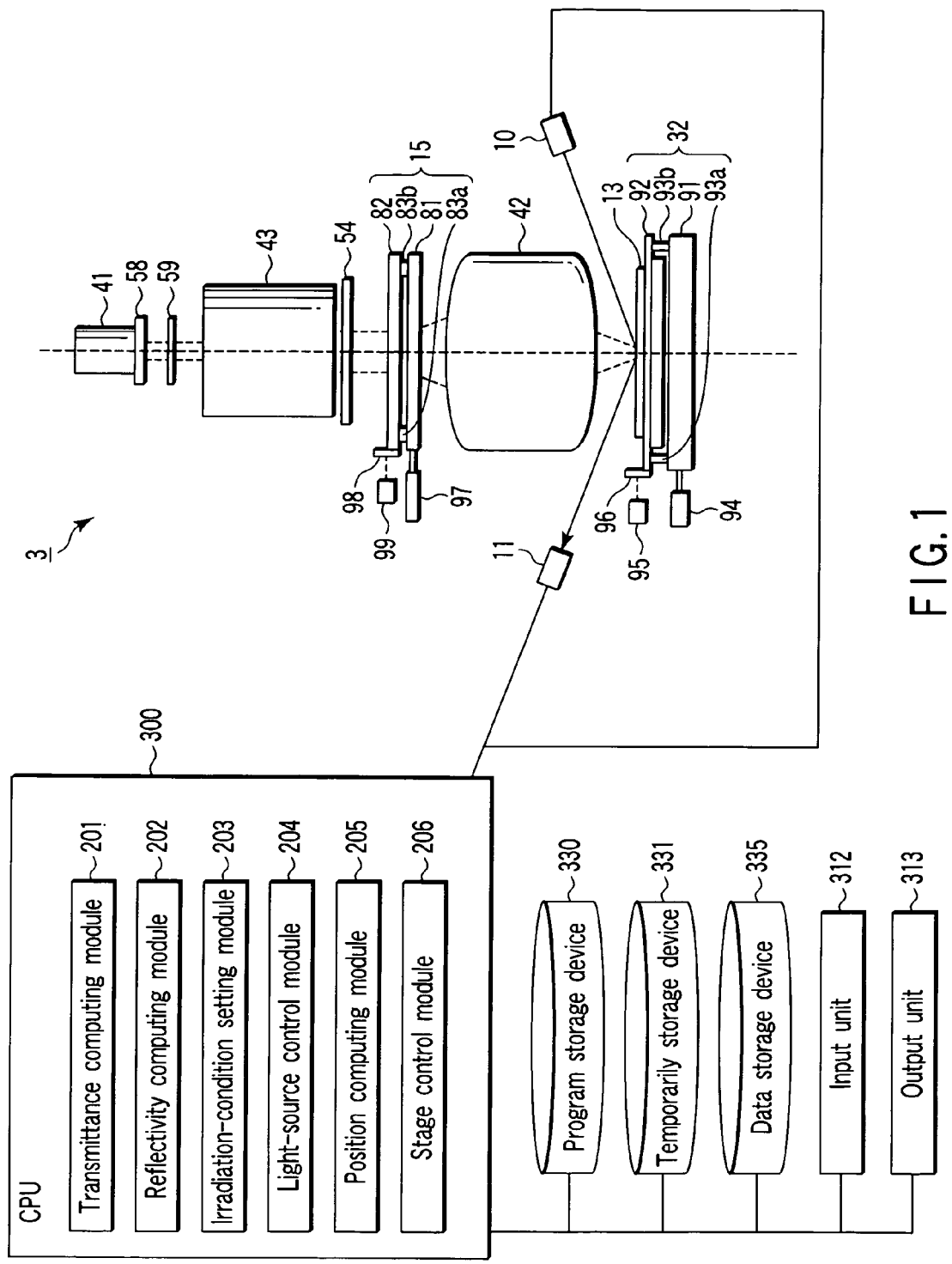
FIG. 1 is a block diagram showing a surface position measuring system to be installed to an exposure apparatus according to an embodiment of the present invention.

Referring to FIG. 1, there is shown a surface position measuring system according to an embodiment of the present invention. As shown, the surface position measuring system includes a central processing unit (CPU) 300. The CPU 300 includes a reflectivity computing module 202 for computing predictive reflectivities of a plurality of circuit patterns provided above a wafer 13 made of silicon (Si) or the like from the design data of a photomask used when a plurality of circuit patterns are formed. In addition, the surface position measuring system includes an inspection light source 10 which irradiates an inspection light to each of a plurality of inspection areas, area by area, of an on-circuit resist film provided above the plurality of circuit patterns under irradiation conditions determined based on a corresponding each of the predictive reflectivities of the plurality of circuit patterns, and a photodetector 11 which detects the inspection light reflected from each of the plurality of inspection areas in order to detect the position of the on-circuit resist film to a focal point of a projection optical system 42 of an exposure apparatus 3 for exposing the on-circuit resist film.

Figure 2:
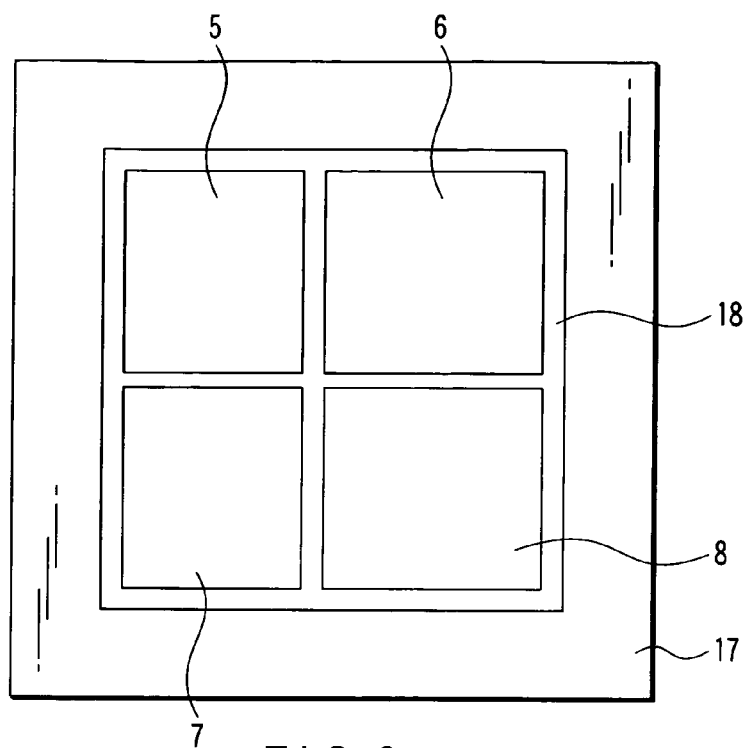
FIG. 2 is a top view showing a first photomask according to the embodiment of the present invention.

The exposure apparatus 3 includes an illumination light source 41 which emits illumination light, an aperture-stop holder 58 provided under the illumination light source 41, a polarizer 59 for polarizing the illumination light, a condensing optical system 43 for condensing the illumination light, a slit holder 54 provided under the condensing optical system 43, and a reticle stage 15, provided under the slit holder 54, for holding a photomask to be irradiated with the illumination light. The photomask, as shown in FIG. 2, includes a transparent mask substrate 18 made of silica glass or the like, a light-shielding film 17 provided on the mask substrate 18, and a plurality of mask patterns 5, 6, 7 and 8, which are provided on the mask substrate 18 and surrounded by the light-shielding film 17. The light-shielding film 17 is made of chromium (Cr), for example. A light shielding material such as Cr, or a semitransparent material such as molybdenum silicide (MoSi), is provided on the mask substrate 18 in each of the mask patterns 5, 6, 7 and 8. The coverage rates of the light shielding material or the semitransparent material in the mask patterns 5, 6, 7 and 8 on the mask substrate 18 are different from one another. Accordingly, the illumination light transmittances of the mask patterns 5, 6, 7 and 8 are different from one another.

The reticle stage 15 for holding the photomask shown in FIG. 1 includes an XY stage 81 for reticle and a Z-inclining stage 82 for reticle, which is coupled to the XY stage 81 by movable shafts 83a and 83b for reticle provided on the XY stage 81. A reticle stage driver 97 is coupled to the reticle stage 15. The reticle stage driver 97 scans the XY stage 81 in the horizontal direction. In addition, the reticle stage driver 97 drives the movable shafts 83a and 83b in the vertical direction. The Z-inclining stage 82 is positioned in the horizontal direction by means of the XY stage 81, and inclinable with respect to the horizontal plane by means of the movable shafts 83a and 83b. A movable mirror 98 for reticle is provided at one side of the Z-inclining stage 82. A position of the Z-inclining stage 82 is measured by a laser interferometer 99 for reticle, which is provided in confrontation with the movable mirror 98.

Further, the exposure apparatus 3 includes the projection optical system 42 which is provided under the reticle stage 15 and projects the mask patterns 5, 6, 7 and 8 formed on the first photomask, and a wafer stage 32 which is provided under the projection optical system 42 and holds the wafer 13. The wafer stage 32 includes an XY stage 91 for wafer and a Z-inclining stage 92 for wafer coupled to the XY stage 91 by movable shafts 93a and 93b for wafer provided on the XY stage 91. A wafer stage driver 94 is coupled to the wafer stage 32. The wafer stage driver 94 scans the XY stage 91 in the horizontal direction. In addition, the wafer stage driver 94 drives the movable shafts 93a and 93b in the vertical direction. The Z-inclining stage 92 is positioned in the horizontal direction by means of the XY stage 91, and inclinable with respect to the horizontal plane by means of the movable shafts 93a and 93b. A movable mirror 96 for wafer is provided at one side of the Z-inclining stage 92. A position of the Z-inclining stage 92 is measured by a laser interferometer 95 for wafer, which is provided in confrontation with the movable mirror 96.

Figure 3:
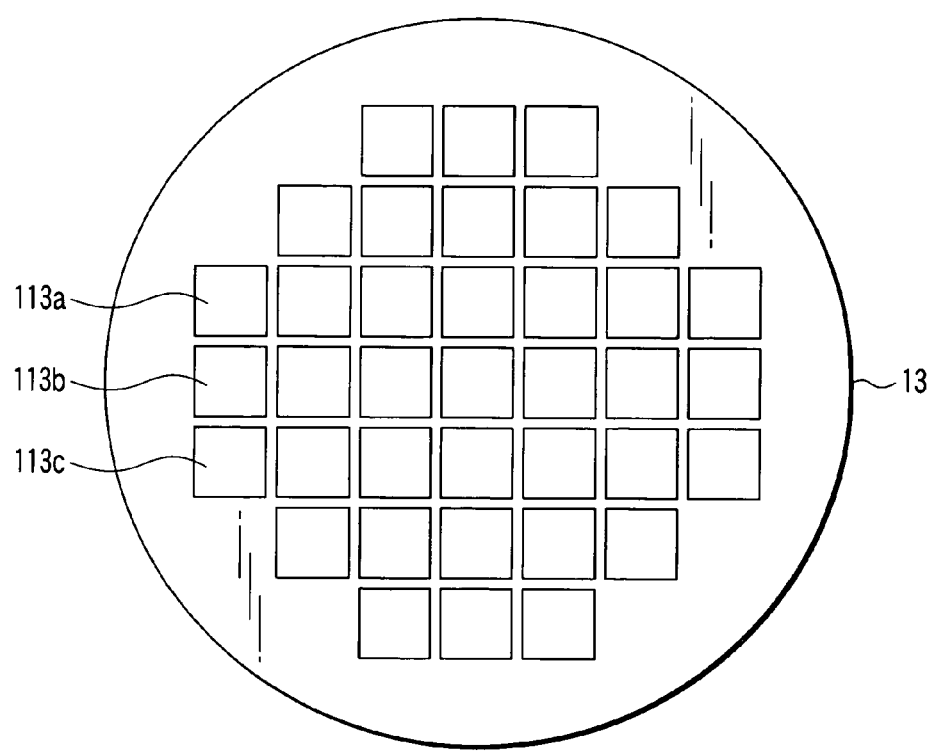
FIG. 3 is a top view showing a wafer according to the embodiment of the present invention.

Transistors, for example, are formed in the wafer 13 held by the wafer stage 32, and a first interlayer insulating film made of silicon nitride (SiN), for example, is formed on the surface of the wafer 13. A circuit-forming resist film made of positive photo-resist or the like is formed on the surface of the first interlayer insulating film. The exposure apparatus 3 reduction-projects the images of the mask patterns 5 to 8 provided on the first photomask shown in FIG. 2 onto a plurality of exposure areas 113a, 113b, 113c, . . . defined on the surface of the circuit-forming resist film above the wafer 13 shown in FIG. 3, while moving the reticle stage 15 and the wafer stage 32. FIG. 3 is viewed through the first interlayer insulating film and the circuit-forming resist film.

A plurality of resist patterns are formed on the surface of the first interlayer insulating film by developing the circuit-forming resist film onto which the images of the mask patterns 5 to 8 shown in FIG. 2 have been projected. The plurality of resist patterns correspond to the mask patterns 5 to 8, respectively. The first interlayer insulating film is selectively removed by dry etching process or the like. In this process step, those resist patterns are used as etching masks. Metal wiring made of copper (Cu) or the like is embedded in the areas from which the first interlayer insulating film has been removed. As a result, a plurality of circuit patterns 45, 46, 47 and 48 shown in FIG. 4, which respectively correspond to the plurality of mask patterns 5 to 8, are formed above the wafer 13. Further, a second interlayer insulating film made of SiN or the like is formed on the circuit patterns 45, 46, 47 and 48, and an on-circuit resist film, e.g., a positive resist film, is formed on the surface of the second interlayer insulating film.

A transmittance computing module 201 of the CPU 300 shown in FIG. 1 computes the transmittances of the mask patterns 5 to 8 shown in FIG. 2 to the illumination light emitted from the illumination light source 41 of the exposure apparatus 3 shown in FIG. 1 from the design data of the mask patterns 5 to 8 shown in FIG. 2.

Figure 4:
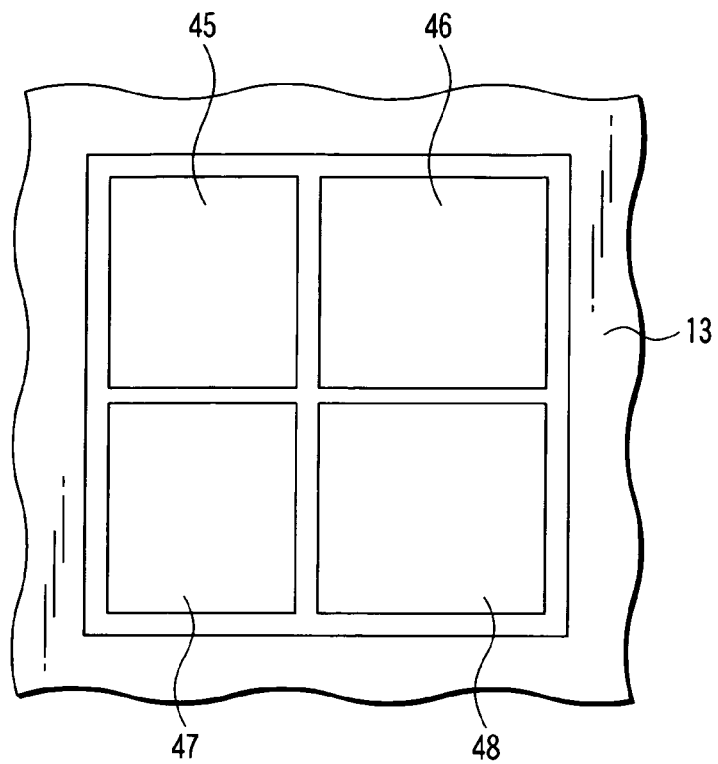
FIG. 4 is a top view showing a plurality of circuit patterns according to the embodiment of the present invention.
Figure 5:
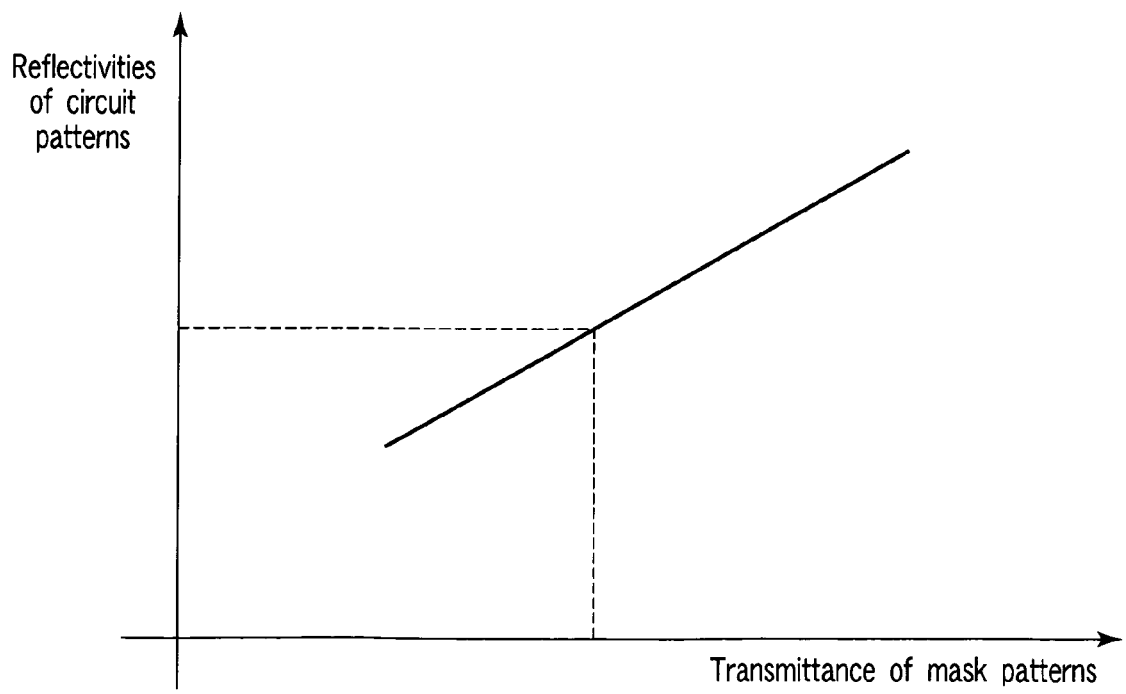
FIG. 5 is a graph showing a relationship between the light transmittance of a mask pattern and the reflectivity of a circuit pattern according to the embodiment of the present invention.

The reflectivities of the circuit patterns 45 to 48 shown in FIG. 4 to the inspection light emitted from the inspection light source 10 shown in FIG. 10 increase with increase in the occupation ratio of the metal wiring embedded in the first interlayer insulating film on the wafer 13. The metal wiring is embedded in the areas from which the first interlayer insulating film has been removed by using the plurality of resist patterns as the etching mask. The plurality of resist patterns are formed by projecting the images of the mask patterns 5 to 8 shown in FIG. 2 on the circuit-forming resist film and then developing the circuit-forming resist film. Accordingly, the correlation as shown in FIG. 5 exists between the transmittances of the mask patterns 5 to 8 and the reflectivities of the circuit patterns 45 to 48. The reflectivity computing module 202 shown in FIG. 1 computes predicted reflectivities of the circuit patterns 45 to 48 from the transmittances of the mask patterns 5 to 8, by using the correlation shown in FIG. 5, which is acquired in advance. The reflectivity computing module 202 shown in FIG. 1 computes predictive reflectivities of the circuit patterns 45 to 48 under irradiation conditions such as a light intensity, an incidence angle and a wavelength of the inspection light incident on the circuit patterns 45 to 48.

An irradiation-condition setting module 203 shown in FIG. 1 sets irradiation conditions of the inspection light irradiated to the plurality of inspection areas on the surface of the on-circuit resist film above the circuit patterns 45 to 48, on the basis of the predictive reflectivities of the circuit patterns 45 to 48 shown in FIG. 4. The irradiation-condition setting module 203 lowers the light intensity of the inspection light irradiated onto the inspection area or areas above one or more of the circuit patterns 45 to 48, which have the predictive reflectivity higher than those of the remaining circuit patterns, below the light intensity of the inspection light irradiated to the inspection areas above the remaining circuit patterns. By adjusting the light intensities of the inspection light irradiated onto the inspection areas above the circuit patterns 45 to 48 in this manner, the light intensities of the inspection light reflected from the inspection areas above the circuit patterns 45 to 48 may be made equal to one another.

When the inspection light is an S-polarization light, the reflectivities of the inspection light of the circuit patterns 45 to 48 increase in increase of the angle of incidence of the inspection light. Therefore, the angle of incidence of the inspection light irradiated onto the inspection area or areas above one or more of the circuit patterns 45 to 48, which have the predictive reflectivity higher than those of the remaining circuit patterns, is set to be smaller than the angle of incidence of the inspection light irradiated to the inspection areas above the remaining circuit patterns. By adjusting the angle of incidence of the inspection light irradiated onto the inspection areas above the circuit patterns 45 to 48, the reflectivities of the inspection light in the inspection areas above the circuit patterns 45 to 48 may be made equal to one another.

There are two cases with regard to the reflectivities of the inspection light in the inspection areas above the circuit patterns 45 to 48. In one case, the reflectivities of the inspection light increase, as the wavelength of the inspection light becomes longer. In the other case, the reflectivities of the inspection light decrease, as the wavelength of the inspection light becomes longer. The increase and decrease of the reflectivities of the inspection light depend on the thickness of the circuit-forming resist film. In the former case where the reflectivities of the inspection light in the inspection areas above the circuit patterns 45 to 48 increase with increase in the wavelength of the inspection light, the irradiation-condition setting module 203 adjusts the wavelength of the inspection light irradiating the inspection area or areas above one or some of the circuit patterns 45 to 48, which have the predictive reflectivity higher than those of the remaining circuit patterns, to be shorter than that of the inspection light irradiating the inspection areas above the remaining circuit patterns. By adjusting the wavelength of the inspection light irradiating the inspection areas above the circuit patterns 45 to 48 in this manner, the reflectivities of the inspection light in the inspection areas above the circuit patterns 45 to 48 may be made equal to one another.

In the irradiation-condition setting module 203, only one of the light intensity, angle of incidence and wavelength of the inspection light at the plurality of inspection areas may be set as the irradiation conditions. Alternatively, in the irradiation-condition setting module 203, any combination of the light intensity, angle of incidence and wavelength of the inspection light at the plurality of inspection areas may be set as the irradiation conditions. The irradiation-condition setting module 203 forms, for example, an irradiation condition table in which the light intensity, angle of incidence, wavelength, and irradiation range of the inspection light at the plurality of inspection areas are described as shown in FIG. 6.

A light-source control module 204 of the CPU 300 shown in FIG. 1 controls the light intensity, the angle of incidence to the wafer 13, and the wavelength of the inspection light emitted from the inspection light source 10, and also controls the irradiation range of the wafer 13 according to the irradiation conditions set by the irradiation-condition setting module 203. A position computing module 205 of the CPU 300 computes measured values of the positions on the surfaces of the plurality of inspection areas on the wafer 13 to the focal position of the projection optical system 42 in the optical axis direction of the projection optical system 42 on the basis of the inspection light detected by the photodetector 11.

A stage control module 206 computes differences between the focal position of the projection optical system 42 and the measured values of the positions on the surfaces of the plurality of inspection areas in the optical axis direction of the projection optical system 42. When the difference is larger than the focal depth of the projection optical system 42, the stage control module 206 drives the wafer stage driver 94 and the movable shafts 93a and 93b for wafer to move the positions of the surfaces of the plurality of inspection areas to the focal position of the projection optical system 42.

Figures 6, 7:
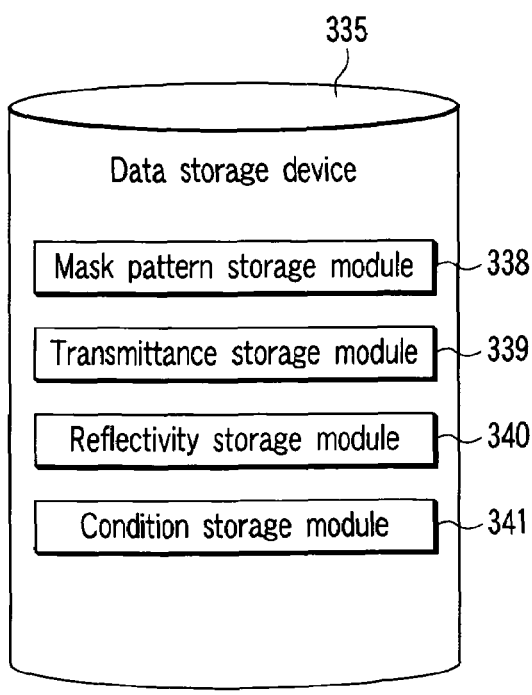
FIG. 6 is a table in which irradiation conditions according to the embodiment of the present invention are recorded.
FIG. 7 is a schematic diagram showing a data storing device according to the embodiment of the present invention.

A data storage device 33, as shown in FIG. 7, includes a mask pattern storage module 338, a transmittance storage module 339, a reflectivity storage module 340, and a condition storage module 341. The mask pattern storage module 338 stores design data of the mask patterns 5 to 8 of the first photomask shown in FIG. 2 in the form of a CAD file or the like. The transmittance storage module 339 shown in FIG. 7 stores the transmittances of the mask patterns 5 to 8 shown in FIG. 2, which are computed by the transmittance computing module 201 shown in FIG. 1. The reflectivity storage module 340 shown in FIG. 7 stores the predictive reflectivities of the circuit patterns 45 to 48 shown in FIG. 4, which are computed by the reflectivity computing module 202 shown in FIG. 1. The condition storage module 341 shown in FIG. 7 stores the irradiation condition table shown in FIG. 6, which is determined by the irradiation-condition setting module 203 shown in FIG. 1.

Further, an input unit 312, an output unit 313, a program storage device 330, and a temporary storage device 331 are further connected to the CPU 300 shown in FIG. 1. A keyboard, a mouse or the like may be used as the input unit 312. A monitor screen using a liquid crystal display (LCD) device or light-emitting diodes (LED) may be used as the output unit 313. The program storage device 330 stores a program which causes the CPU 300 to perform the data transmission and reception to and from the device connected to the CPU 300. The temporary storage device 331 temporarily stores data during the course of computing process by the CPU 300.

An exposure method according to the embodiment of the present invention will be described by using a flow chart shown in FIG. 8. The computation results of the computing operation by the CPU 300 shown in FIG. 1 are sequentially stored in the temporary storage device 331.

(a) In step S101, a first interlayer insulating film is formed on the wafer 13. By using a coating apparatus such as a spin coater, a surface of the first interlayer insulating film on the wafer 13 is coated with photoresist to form a circuit-forming resist film. In step S102, a first photomask shown in FIG. 2 is set in the reticle stage 15 of the exposure apparatus 3, and the wafer 13 having the circuit-forming resist film formed thereon is set in the wafer stage 32 shown in FIG. 1. The first photomask is irradiated with illumination light to project images of mask patterns 5 to 8 provided on the first photomask onto the circuit-forming resist film.

(b) In step S103, the circuit-forming resist film on the wafer 13 is post-exposure baked (PEB) by using a heater or the like. Following the post-exposure bake process, the circuit-forming resist film on the wafer 13 is developed with a developing device to form a plurality of resist patterns corresponding to the mask patterns 5 to 8 on the first interlayer insulating film. In step S104, the first interlayer insulating film is selectively etched away by anisotropic etching process. In this process step, the plurality of resist patterns are each used as an etching mask. Copper (Cu), for example, is embedded in the areas from which the first interlayer insulating film has been removed, to thereby form circuit patterns 45 to 48 above the wafer 13 shown in FIG. 4.

(c) In step S105, the transmittance computing module 201 reads out the design data of the mask patterns 5 to 8 which are provided on the first photomask shown in FIG. 2, from the mask pattern storage module 338 shown in FIG. 7. The transmittance computing module 201 shown in FIG. 1 computes transmittances of the mask patterns 5 to 8 to the illumination light. The transmittances computed by the transmittance computing module 201 are stored in the transmittance storage module 339 shown in FIG. 7.

(d) In step S106, the reflectivity computing module 202 shown in FIG. 1 reads out the transmittances of the mask patterns 5 to 8 from the transmittance storage module 339. Then, the reflectivity computing module 202 computes predictive reflectivities of the circuit patterns 45 to 48, which are formed by projecting the mask patterns 5 to 8 on the circuit-forming resist film, to inspection light by using the transmittance-reflectivity correlation shown in FIG. 5. The predictive reflectivities of the circuit patterns 45 to 48 computed by the reflectivity computing module 202 are stored in the reflectivity storage module 340 shown in FIG. 7.

(e) In step S107, a second interlayer insulating film is formed on the circuit patterns 45 to 48. Photoresist is applied to the second interlayer insulating film by using a coating apparatus, to thereby form an on-circuit resist film. In step S108, a second photomask having a mask pattern, which is different from that of the first photomask, is placed on the reticle stage 15 of the exposure apparatus 3 shown in FIG. 1. The wafer 13 having the on-circuit resist film formed thereon is placed on the wafer stage 32. In step S109, the irradiation-condition setting module 203 reads out the predictive reflectivities of the circuit patterns 45 to 48 from the reflectivity storage module 340. Then, the irradiation-condition setting module 203 computes irradiation conditions such as the angle of incidence, wavelength, and intensity of the inspection light emitted from the inspection light source 10 onto the on-circuit resist film, on the basis of the predictive reflectivities of the circuit patterns 45 to 48. The irradiation conditions computed by the irradiation-condition setting module 203 are stored in the condition storage module 341 shown in FIG. 7.

(f) In step S110, the light-source control module 204 shown in FIG. 1 reads out the irradiation conditions from the condition storage module 341 and controls the light intensity, angle of incidence, wavelength, irradiation range, and the like of the inspection light emitted from the inspection light source 10. In step S111, the inspection light source 10 irradiates an inspection light onto each of a plurality of inspection areas, area by area, of the on-circuit resist film above the circuit patterns 45 to 48, according to the inspection conditions. The photodetector 11 detects the inspection light reflected from the plurality of inspection areas of the on-circuit resist film. Following this, the position computing module 205 computes measured values of the positions on the surfaces of the plurality of inspection areas of the on-circuit resist film on the basis of the inspection light detected by the photodetector 11.

(g) In step S112, the stage control module 206 drives the wafer stage driver 94 and the movable shafts 93a and 93b for wafer to move the position of the surface of the on-circuit resist film to the focal position of the projection optical system 42, on the basis of the measured values of the positions of the surface of the on-circuit resist film computed by the position computing module 205. In step S113, the illumination light source 41 of the exposure apparatus 3 irradiates the second photomask with illumination light. As a result, the on-circuit resist film is exposed to the illumination light having passed through the mask patterns provided on the second photomask, thereby completing the exposure method according to the embodiment.

The conventional surface position measuring system has the following disadvantage. In the case where the inspection light is irradiated to the inspection areas above the circuit patterns 45 to 48 shown in FIG. 4, the different reflectivities of the circuit patterns 45 to 48 will occur and adversely affect the detection of the surface positions of the inspection areas. In this connection, it is noted that in the surface position measuring system of the embodiment, the intensity of the inspection light emitted from the inspection light source 10 is set so that the intensities of the inspection light reflected from the circuit patterns 45 to 48 are equal to one another. Therefore, the different reflectivities of the circuit patterns 45 to 48 do not adversely affect the detection of the surface positions of the inspection areas.

Also, in the surface position measuring system of the embodiment, the angle of incidence to the wafer 13 of the inspection light emitted from the inspection light source 10 shown in FIG. 1 is set so that the reflectivities of the inspection light to the circuit patterns 45 to 48 shown in FIG. 4 are equal to one another. Therefore, the surface position measuring system of the embodiment successfully eliminates the adverse effect of the different reflectivities of the circuit patterns 45 to 48, which is caused when the angle of incidence is fixed. Further, in the surface position measuring system of the embodiment, the wavelength of the inspection light emitted from the inspection light source 10 shown in FIG. 1 is set so that the reflectivities of the inspection light of the circuit patterns 45 to 48 shown in FIG. 4 are equal to one another. Therefore, the surface position measuring system of the embodiment successfully eliminates the adverse effect of the different reflectivities of the circuit patterns 45 to 48, which is caused when the wavelength is fixed.

While some embodiments of the present invention have been described, it should be understood that the invention is not limited to the descriptions and drawings attached. In the embodiment, the reflectivity computing module shown in FIG. 1 computes the predictive reflectivities of the circuit patterns 45 to 48 shown in FIG. 4 from the light transmittances of the mask patterns 5 to 8 shown in FIG. 2. If required, in the embodiment, the reflectivity computing module shown in FIG. 1 may compute the predictive reflectivities of the circuit patterns 45 to 48 shown in FIG. 4 from the coverage of the light-shielding film or semitransparent material on the mask substrate 18 of each of the mask patterns 5 to 8 shown in FIG. 2. The process steps S105 and S106 in FIG. 8 may be carried out at any time before the process step S107 is carried out.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A surface position measuring system comprising:
   a reflectivity computing module which computes predictive reflectivities of a plurality of circuit patterns;
   an inspection light source which irradiates an inspection light onto each of a plurality of inspection areas, area by area, above the plurality of circuit patterns under irradiation conditions determined based on a corresponding each of the predictive reflectivities of the plurality of circuit patterns; and
   a photodetector which detects a reflected inspection light reflected from each of the plurality of inspection areas to detect a surface position of a corresponding each of the plurality of inspection areas.

2. A surface position measuring system according to claim 1, wherein the predictive reflectivities of the plurality of circuit patterns are computed from design data of a plurality of mask patterns of a photomask used when the plurality of circuit patterns are formed.

3. A surface position measuring system according to claim 1, wherein the plurality of inspection areas includes a plurality of areas on a resist film formed on the plurality of circuit patterns through an interlayer insulation film.

4. A surface position measuring system according to claim 1, wherein the irradiation conditions include at least one of an intensity, an incidence angle and a wave length of the inspection light irradiated onto the plurality of inspection areas.

5. A surface position measuring system according to claim 4, wherein the irradiation conditions further include an irradiation range of the inspection light irradiated onto the plurality of inspection areas.

6. A surface position measuring system according to claim 4, wherein the intensity of the inspection light irradiated onto the inspection area or areas above one or more of the circuit patterns, which have the predictive reflectivity higher than those of remaining circuit patterns, is set to be lower than the intensity of the inspection light irradiated to the inspection areas above remaining circuit patterns.

7. A surface position measuring system according to claim 4, wherein when the inspection light is an S-polarization light, the incidence angle of the inspection light irradiated onto the inspection area or areas above one or more of the circuit patterns, which have the predictive reflectivity higher than those of the remaining circuit patterns, is set to be smaller than the incidence angle of the inspection light irradiated to the inspection areas above the remaining circuit patterns.

8. A surface position measuring system according to claim 4, wherein when the reflectivities of the inspection light from the inspection areas above the circuit patterns increase with increase in the wavelength of the inspection light, the wavelength of the inspection light irradiated onto the inspection area or areas above one or more of the circuit patterns, which have the predictive reflectivity higher than those of the remaining circuit patterns, is set to be shorter than that of the inspection light irradiated onto the inspection areas above the remaining circuit patterns.

9. A surface position measuring system according to claim 1, further comprising a light-source control module which controls the inspection light source according to the irradiation conditions.

10. A surface position measuring system according to claim 1, further comprising a position computing module which computes measured values of the surface positions of the plurality of inspection areas to a focal position of a projection optical system on the basis of the reflected inspection light detected by the photodetector.

11. A surface position measuring system according to claim 10, further comprising a stage control module which performs a control so that the surface positions of the plurality of inspection areas are moved to the focal position of the projection optical system according to differences between the focal position of the projection optical system and the measured values of the surface positions of the plurality of inspection areas.

12. A surface position measuring system according to claim 1, further comprising a transmittance computing module which computes transmittances of the mask patterns to the illumination light emitted from the illumination light source of an exposure apparatus from the design data of the mask patterns of the photomask.

13. An exposure method comprising:
projecting images of a plurality of mask patterns provided on a photomask onto a circuit-forming resist film provided on a wafer;
developing the circuit-forming resist film to form a plurality of resist patterns on the wafer;
forming a plurality of circuit patterns on the wafer, with use of the plurality of resist patterns;
obtaining predictive reflectivities of the plurality of circuit patterns;
forming an on-circuit resist film on the plurality of circuit patterns;
irradiating an inspection light to each of a plurality of inspection areas, area by area, of the on-circuit resist film, which are above the plurality of circuit patterns, under irradiation conditions determined based on a corresponding each of the predictive reflectivities of the plurality of circuit patterns,
detecting a reflected inspection light reflected from each of the plurality of inspection areas,
detecting a surface position of each of the plurality of inspection areas to a projection optical system of an exposure apparatus which irradiates an illumination light to expose the on-circuit resist film, based on the reflected inspection light reflected from a corresponding each of the plurality of inspection areas,
moving the wafer to position each of the surface positions of the plurality of inspection areas at a focal point of the projection optical system of the exposure apparatus, and
irradiating an illumination light to expose the on-circuit resist film.

14. An exposure method according to claim 13, wherein obtaining the predictive reflectivities of the plurality of circuit patterns includes obtaining the predictive reflectivities of the plurality of circuit patterns from design data of the plurality of mask patterns of the photomask.

15. An exposure method according to claim 13, wherein obtaining the predictive reflectivities of the plurality of circuit patterns includes computing transmittances of the plurality of mask patterns of the photomask to an illumination light irradiated by an illumination light source of the exposure apparatus from design data of the plurality of mask patterns and obtaining the predictive reflectivities of the plurality of circuit patterns from the computed transmittances of the plurality of mask patterns, using a correlation of the transmittances and predictive reflectivities.

16. An exposure method according to claim 15, wherein the relationship of the transmittances and predictive reflectivities shows a proportional characteristics.

17. An exposure method according to claim 13, wherein obtaining the predictive reflectivities of the circuit patterns includes obtaining the predictive reflectivities from coverage rates of light-shielding films or semitransparent films of the plurality of mask patterns of the photomask.

18. An exposure method according to claim 13, wherein the irradiation conditions include at least one of an intensity, an incidence angle and a wave length of the inspection light irradiated onto the plurality of inspection areas.

19. An exposure method according to claim 13, wherein obtaining the predictive reflectivities of the circuit patterns is carried out before forming the on-circuit resist film above the plurality of circuit patterns.

20. A semiconductor device manufacturing method of manufacturing a semiconductor device, in which the exposure method claimed in claim 13 is used.

* * * * *

UNITED STATES PATENT AND TRADEMARK OFFICE
CERTIFICATE OF CORRECTION

PATENT NO. : 7,710,583 B2
APPLICATION NO. : 11/907190
DATED : May 4, 2010
INVENTOR(S) : Kono It is certified that error appears in the above-identified patent and that said Letters Patent is hereby corrected as shown below:

In the Claims:

Claim 4, column 9, line 12, change "wave length" to --wavelength--.

Claim 16, column 10, line 49, change "shows a" to --shows--.

Claim 18, column 10, line 57, change "wave length" to --wavelength--.

Signed and Sealed this
Eleventh Day of June, 2013

Teresa Stanek Rea
*Acting Director of the United States Patent and Trademark Office*